United States Patent [19]

Nakanishi et al.

[11] Patent Number: 5,582,818
[45] Date of Patent: Dec. 10, 1996

[54] ULTRAVIOLET SCREENING POWDER AND COSMETICS

[75] Inventors: Noriyuki Nakanishi, Kawasaki; Hiroo Mori, Ichihara, both of Japan

[73] Assignees: Ajinomoto Co., Inc.; Asahi Glass Co., Ltd., both of Tokyo, Japan

[21] Appl. No.: 379,953

[22] Filed: Jan. 27, 1995

[30] Foreign Application Priority Data

Jan. 27, 1994 [JP] Japan .................... 6-007546

[51] Int. Cl.⁶ .................. A61K 7/42; C01G 9/02
[52] U.S. Cl. .................. 424/59; 423/622; 424/60; 424/63; 424/69
[58] Field of Search .................. 423/622; 424/63, 424/69, 59, 60

[56] References Cited

U.S. PATENT DOCUMENTS

| | | | |
|---|---|---|---|
| 4,606,914 | 8/1986 | Miyoshi | 514/789 |
| 4,659,562 | 4/1987 | Arraudeau et al. | 424/63 |
| 4,839,163 | 6/1989 | Busch, Jr. | 424/63 |
| 4,857,307 | 8/1989 | Suss et al. | 424/63 |
| 5,039,518 | 8/1991 | Barone et al. | |
| 5,199,979 | 4/1993 | Lin et al. | 106/287.14 |

FOREIGN PATENT DOCUMENTS

| | | |
|---|---|---|
| 0462709 | 12/1991 | European Pat. Off. . |
| 0489657 | 6/1992 | European Pat. Off. . |
| 60-67565 | 4/1985 | Japan . |
| 0109510 | 6/1985 | Japan .................... 424/63 |
| 1078709 | 4/1986 | Japan .................... 424/69 |
| 1069708 | 4/1986 | Japan .................... 424/63 |
| 63-3078 | 1/1988 | Japan . |
| 5-186706 | 7/1993 | Japan . |

OTHER PUBLICATIONS

Database WPI, Derwent Publications, AN 86–116717 [18], JP 61 057 653, Mar. 24, 1986.
Patent Abstracts of Japan, vol. 12, No. 333 (C–526), JP 63 093707, Apr. 25, 1988.
Cosmetics and Toiletries, vol. 107, No. 8, pp. 85–90, Aug. 1992, L. Armanini, et al., "Evaluation of Feel: Lauroyl Lysine Treated Pigments".
Database WPI, Derwent Publications, AN 86–133796 [21], JP 61 069 709, Apr. 10, 1986.

Primary Examiner—Shelley A. Dodson
Attorney, Agent, or Firm—Oblon, Spivak, McClelland, Maier & Neustadt, P.C.

[57] ABSTRACT

Herein disclosed are cosmetics having spherical silica containing an ultraviolet reflecting meterial surface-treated with platy N-lauroyl-L-lysine incorporated therein. According to the present invention, those cosmetics having spherical silica containing a conventional ultraviolet reflecting material blended therewith are improved in cosmetic functions such as spreadability upon application, lubricity upon application, smooth feeling on skins, adhesiveness to skins, water repellency, feeling, etc., maintaining the original ultraviolet screening effect.

4 Claims, No Drawings

ULTRAVIOLET SCREENING POWDER AND COSMETICS

BACKGROUND OF THE INVENTION

1. Field of the Invention

The present invention concerns an ultraviolet screening powder and cosmetics and, more in particular, an ultraviolet screening powder having good lubricity and water repellency, as well as cosmetics containing such a powder.

2. Discussion of the Background

Heretofore, an ultraviolet reflecting agent has been mixed into cosmetics with an aim of protecting skins against ultraviolet rays. And, as such ultraviolet reflecting agents, titanium oxide, zinc oxide, cerium oxide and the like have been used.

Titanium oxide has a refractive index of as large as 2.5 and shows a high ultraviolet screening effect (ultraviolet reflecting effect), but involves the problem that cosmetics mixed with titanium oxide are whitened upon application and give no natural feeling of make-up. Further, ultra-fine particles of titanium oxide that cause less scattering in the visible light region have also been used, but they have the problem of being coagulated upon preparation of cosmetics since the grain size is too small, which results in deterioration of the ultraviolet protecting effect of cosmetics mixed therewith. Further, since such titanium oxide as referred-to above has no defined particular shape, it shows poor lubricity upon skin application to bring about a problem with respect to the feeling in use.

Finely particulate zinc oxide and cerium oxide are also difficult to be prevented from being coagulated upon preparation of cosmetics having such an oxide blended therewith, and such cosmetics involve a problem with respect to the feeling upon application.

For improving the feeling in use, it has been proposed, for example, to coat the surfaces of spherical silica beads with titanium oxide (Japanese Patent Application Laid-Open (kokai) No. 57653/'86).

Furthermore, such oxides as described above are highly hydrophilic, and cosmetics having them blended therewith are wetted with water or sweat upon application onto skins, which results in a problem with respect to water repellency which, in turn, results in sweat bleeding, make-up bleeding and the like problems.

SUMMARY OF THE INVENTION

Accordingly, it is an object of the present invention to provide an ultraviolet screening powder of excellent spreadability, lubricity, smooth feeling and adhesiveness as well as excellent water repellency, and ultraviolet screening cosmetics having such an excellent powder incorporated therein and giving good spreadability upon application, good lubricity upon application, good smooth feeling on skins, good adhesiveness to skins, and good water repellency and thus water proofness to exhibit an excellent effect of preventing make-up bleeding and the like and provide good feeling.

The present invention thus provides an excellent ultraviolet screening powder as well as cosmetics comprising such a powder as an essential ingredient, which satisfy the above object of the invention and other objects which will become apparent from the description of the invention given hereinbelow.

In an aspect of the present invention, there is provided an ultraviolet screening powder in respect of which the constituent particles are silica spheres containing an ultraviolet reflecting material and surface-treated with platy N-lauroyl-L-lysine.

In another aspect of the present invention, there is provided the ultraviolet screening powder as set forth above, wherein said ultraviolet reflecting material is a metal oxide.

In a third aspect of the present invention, there is provided the ultraviolet screening powder as set forth just above, wherein said metal oxide is an oxide selected from titanium oxide, zinc oxide and cerium oxide or two or more of them used in combination.

And, in a fourth aspect of the present invention, there are provided cosmetics comprising as an essential ingredient any one of the ultraviolet screening powders as set forth above.

DETAILED DESCRIPTION OF THE INVENTION

As a result of an earnest study for attaining the foregoing objects, the present inventors have found that the foregoing objects can be attained with silica spheres (i.e., spherical silica) containing an ultraviolet reflecting material and surface-treated with platy N-lauroyl-L-lysine, and have accomplished the present invention on the basis of these findings.

First of all, the present invention concerns an ultraviolet screening powder whose constituent particles are silica spheres containing an ultraviolet reflecting material and surface-treated with platy N-lauroy-L-lysine.

Description will be made first with respect to the ultraviolet reflecting materials. As the ultraviolet reflecting material, a metal oxide such as, e.g., titanium oxide, zinc oxide or cerium oxide can be preferably used. Combination of two or more of the materials such as titanium and cerium oxides or titanium and zinc oxides is particularly preferred since the wavelength region of ultraviolet light to be absorbed or screened is widened.

Next, description will be given of the silica spheres or spherical silica to be used for the present invention.

The particle size of the silica spheres has no particular restriction, but their mean or average particle diameter is desirably from 1 to 50 µm when they are incorporated into, or blended with, cosmetics. A mean particle diameter of less than 1 m is not preferred because of the resultant insufficient spreadability and lubricity. A mean particle diameter exceeding 50 µm is nor preferred since it gives gritty feeling. Out of the above-mentioned range of the average particle diameter, 2 to 20 µm is more preferable in view of lubricity upon application. The particle diameter of spherical silica having such a mean particle diameter ranges usually within a range from 0.1 to 200 µm It is desirable that silica has a complete or approximately complete spherical shape since lubricity is improved when it is incorporated in cosmetics, but somewhat deformed spherical shapes may also do so long as the objects of the invention are attainable. In addition, if silica particles of indefinite shapes or pulverizates of the silica spheres are incorporated partially, that gives no troubles so long as the purposes of the invention are attainable.

The silica spheres preferably have a pore volume of from 0.01 to 3 cc/g. It is further preferred that the pore volume of the silica spheres is from 0.5 to 2.5 cc/g. The silica spheres preferably have a surface area of from 5 to 1000 m²/g. It is further preferred that the surface area of the silica spheres is from 100 to 600 m²/g.

There is no particular restriction on the method of manufacturing silica spheres and those manufactured by various methods can be used. For instance, spherical silica can be obtained by forming finely particulate liquid droplets of a silicate in a non-polar organic solvent containing a surface active agent, and then gelling them with gaseous carbon dioxide, followed by washing and drying. According to this method, particles of a uniform grain size, for example, spheres of a mean grain size of about 1 to 10 μm, and suitable to the application use can be manufactured easily (Japanese Patent Publication (kokai) No. 20563/'94)). Further, it can also be obtained by forming liquid droplets of fine particles of a silicate ester in a solvent and then gelling them with ammonia or the like. Furthermore, spherical silica can also be obtained by spray-drying a silica sol.

Further, while spherical silica obtained by the foregoing methods is porous, non-porous silica can also be preferably used. Such non-porous spherical silica can be obtained, for example, by baking spherical or undefined porous silica in a gas stream at an elevated temperature (Japanese Patent Application Laid-Open (kokai) No. 83712/'92).

There is no particular restriction on the method of incorporating such an ultraviolet reflecting material as described above into spherical silica that can be manufactured as described above, i.e., the method of producing silica spheres containing an ultraviolet reflecting material, and various methods may be employed. A method of coating a previously formed spherical silica with a sol containing an ultraviolet reflecting material or a solution from which an ultraviolet reflecting material is deposited upon drying, by means of spraying or the like, or a method of dipping spherical silica into such a sol or solution and then drying the dipped silica is preferred. Alternatively, spherical silica containing an ultraviolet reflecting material can also be obtained by blending an ultraviolet reflecting material or a precursor thereof with the starting material during the manufacturing step of spherical silica.

The amount of the ultraviolet reflecting material to be incorporated into spherical silica by such a method is preferably from 5 to 300% by weight based on the silica moiety. An amount of less than 5% by weight is not preferred since the ultraviolet screening effect may possibly be insufficient. An amount of more than 300% by weight is nor preferred since the ultraviolet screening effect is not increased any more while the ultraviolet reflecting material tends to coagulate with each other to deteriorate the lubricity. A more preferred amount of the ultraviolet reflecting material is from 20 to 100% by weight based on the silica moiety.

Finally, description will be made of the method of treating the surfaces of spherical silica containing an ultraviolet reflecting material that can be manufactured as described above with platy N-lauroyl-L-lysine.

Platy N-lauroyl-L-lysine (i.e., N-lauroyl-L-lysine plates) can be prepared, for example, by heat-dehydrating L-lysine, a basic amino acid, and lauric acid, a long-chained fatty acid, and dissolving the resultant reaction product in an aqueous solvent at a pH of not higher than 2 or a pH of not lower than 11, followed by neutralization and then crystallization. By this method, platy N-lauroyl-L-lysine having a uniform grain size of, for example, about 1 to 30 μm (the grain size of a platy crystal means herein the length of the diagonal line on the plane part) can be easily produced (Japanese Patent Publication (kokoku) No. 25413/'91).

As a method of treating the surface of fine spherical silica containing an ultraviolet reflecting substance (generally, a powder) with N-lauroyl-L-lysine, there can be mentioned, for example, dry and wet methods, either of which can be used. The dry method is a convenient and effective one, for which a mixing/stirring device such as a Henschel mixer, a vibrational ball mill, a rotary ball mill or a super mixer is used. According to this method, the surfaces of the powder can be treated easily, for example, by stirring and mixing an N-lauroyl-L-lysine powder and powdery silica or by mixing N-lauroyl-L-lysine and powdery silica and then copulverizing the mixture. Further, according to the wet method, the surfaces of the powdery silica can be treated, for example, by dissolving N-lauroyl-L-lysine in an organic solvent using calcium chloride as a solubilizer, since N-lauroyl-L-lysine is scarcely soluble in water at about neutral pH or a usual oil, bringing it into contact with the powdery silica, washing the thus handled powder with water to eliminate the calcium chloride, followed by drying. Further, in addition to the dry and the wet methods, a similar surface treatment can also be carried out, for example, by dissolving N-lauroyl-L-lysine in an acidic or alkaline water or aqueous solvent, bringing it into contact with the powdery silica, neutralizing the mass to about neutral pH to crystallize and deposit the N-lauroyl-L-lysine on the surfaces of the powdery silica and washing out the salts resultant from neutralization with water, followed by drying.

The amount of N-lauroyl-L-lysine to be used for the surface treatment of silica spheres containing an ultraviolet reflecting material is preferably from 0.05 to 90% by weight, more preferably from 0.5 to 75% by weight, based on the spherical silica. If it is less than 0.05% by weight, the effect of the surface treatment is not sufficient. On the other hand, if it exceeds 90% by weight, there is no economical merit since the treating effect gives not so much improvement.

Next, the present invention concerns various cosmetics in which an ultraviolet screening powder of the above-described embodiment of the present invention is incorporated.

In the cosmetics of the present invention, conventional ingredients of cosmetics can of course be incorporated, if required in addition to the essential ingredient described above (i.e., an ultraviolet screening powder of the present invention). As such conventional ingredients, there can be mentioned, for example, solid oils, semi-solid oils, liquid oils, moisture keeping agents, emollient agents, water soluble polymers, oleosoluble polymers, various kinds of surface active agents, organic and inorganic pigments, organic and inorganic pigments treated with silicone or fluoro compound, colorants such as organic dyes, ethanol, various kinds of amino acids, preservatives, antioxidants, colors, viscosty improvers, pH adjusters, perfumes, blood flow promoters, cryogenic agents, antiperspirants, sterilizers and skin activators, and they are blended within such a range of quality and quantity where the objects and the effects of the present invention are not deteriorated. Further, ultraviolet absorbents to be detailed later can also be added.

As such solid or semi-solid oils, there can be mentioned, for example, vaseline, lanolin, ceresin, microcrystalline wax, carnauba wax, candelilla wax; higher fatty acids such as coconut oil fatty acid, lauric acid and hardened tallow fatty acid; and higher alcohols such as lauric alcohol, cetyl alcohol, stearyl alcohol and behenyl alcohol. They can be used singly or as an admixture of two or more of them.

As such liquid oils, there can be mentioned, for example, vegetable oils such as avogado oil, olive oil and hohoba oil; fatty acids such as oleic acid and isostearic acid; alcohols such as hexadecyl alcohol and oleyl alcohol; ester oils such as cetyl 2-ethylhexanoate, 2-octyldodecyl myristate, neopentylglycol di-2-ethylhexanoate, glycerol tri-2-ethylhexanoate, 2-octyldodecyl oleate, isopropyl myristate, glycerol triisostearate, 2-ethylhexanoic acid diglyceride, octyldodecyl long chained acyl glutamate; silicone oils such as dimethyl polysiloxane, methyl hydrogen polysiloxane, methylphenyl polysiloxane and octamethyl cyclotetrasiloxane; and liquid hydrocarbon oils such as liquid paraffin, squalene and squalane. They may be used singly or as an admixture of two or more of them.

As such moisture keeping agents, there can be mentioned those moisture keeping agents incorporated generally in cosmetics, such as, for example, sorbitol, mannitol, glycerine, propylene glycol, 1,3-butylene glycol, pyrrolidone carboxylic acid, sodium pyrrolidone carboxylate, lactic acid, sodium lactate, betaine, polyethylene glycol, sodium hyaluronate, polyasparagic acid salts, and water soluble chitin. They may be used alone or in admixture of two or more of them.

As such emollient agents, there can be mentioned, for example, cholesteryl long chained acyl glutamate, cholesteryl hydroxystearate, dipentaerythrite fatty acid ester, cholesteryl ester of lanolin fatty acid. They may be used alone or in admixture of two or more of them.

As such surface active agents, there can be mentioned, for example, nonionic surface active agents such as POE cetyl ether, POE stearic acid ester, POE sorbitan monolaurate, glycerine fatty acid ester, polyglycerine fatty acid ester and polyoxyethylene hardened castor oil; cationic surface active agents such as benzalkonium chloride, stearyl trimethyl ammonium chloride, dicetyl dimethyl ammonium chloride, and behenyl trimethyl ammonium chloride; amphoteric surface active agents such as 2-cocoyl-N-carboxymethyl-N-hydroxyethyl imidazolinium betaine, and amido acetic acid betaine; and anionic surface active agents such as higher alcohol sulfates, higher alcohol ether sulfates, long chained fatty acid alkali metal salts, long chained fatty acid alkaline earth metal salts, long chained fatty acid basic amino acid salts, N-long chained acyl-amino acids, and N-long chained acyl-amino acid salts. They may be used alone or in admixture of two or more of them.

As such water soluble polymers, there can be mentioned those water soluble polymers used generally in cosmetics, such as, for example, carboxymethyl cellulose, methyl cellulose, hydroxymethyl cellulose, polyvinyl alcohol, polyvinyl pyrrolidone, tragachanth gum, carrageenan, dextrin, dextrin fatty acid ester, carboxyvinyl polymer, xanthan gum, gelatin, sodium alginate and gum arabic.

As such oleosoluble polymers, there can be mentioned those oleosoluble polymers used generally for cosmetics, such as, for example, nitrocellulose and high molecular silicone.

As such organic or inorganic pigments, they have no particular restriction so long as they are usually used in cosmetics. And there can be mentioned, for example, inorganic powders such as silicic acid, anhydrous silicic acid, magnesium silicate, talc, sericite, kaolinite, red iron oxide, clay, bentonite, titanium coated mica, bismuth oxychloride, zirconium oxide, magnesium oxide, zinc oxide, titanium oxide, aluminum oxide, calcium sulfate, barium sulfate, magnesium sulfate, calcium carbonate, magnesium carbonate, iron oxide, ultramarine, chromium oxide, chromium hydroxide, calamine and carbon black, and composite products thereof; organic powders such as polyamide, polyester, polypropylene, polystyrene, polyurethane, vinyl resin, urea resin, phenolic resin, fluoro resin, silicone resin, acrylic resin, melamine resin, epoxy resin, polycarbonate resin, divinyl benzene—styrene copolymer, silk powder, cellulose, CI pigment yellow, and CI pigment orange; as well as composite powders of such an inorganic powder and an organic powder. The powders may be used alone or in admixture of two or more of them.

As such ultraviolet absorbents, there can be mentioned, for example, para-amino benzoic acid derivatives such as para-amino benzoic acid and octyl para-dimethylamino benzoate; benzophenone derivatives such as 2-hydroxy-4-methoxy benzophenone and dihydroxydimethoxy benzophenone; methoxy cinnamic acid derivatives such as ethyl para-methoxy cinnamate, and octyl para-methoxy cinnamate; salicylic acid derivatives such as octyl salicylate and homomenthyl salicylate; α-dehydroamino acid derivatives such as 2-ethylhexyl N-benzoyl-O-methyl-α-dehydrotyrosine; benzal hydantion derivatives such as 2-ethylhexyl 4-(3,4-dimethoxyphenyl)-methylene-2,5-dioxo-1-imidazolizine propionate; and urocanic acid, ethyl urocanate, 4-tert-butyl-4'-methoxybenzoyl methane, and 2-(2'-hydroxy-5'-methylphenyl)benzotriazole. They may be used alone or in admixture of two or more or them.

The cosmetics of the present invention can be in the form of powder, liquid, cream, kneaded product, cake, pencil, stick, ointment or the like. Specifically, there can be mentioned, for example, pressed powder, loose powder, eye shadow, cream, lotion, aqueous cosmetics, liquid foundation, anti-sunburn cream, sunburn oil, shampoo, rinse, treatment, hair tonic, hair growing agent, stick pomade, color rinse, solid detergent, liquid detergent, anti-perspirant, bathing agent, shoe cream and ointment.

There is also no particular restriction on the preparation of the cosmetics and, since conventional preparation methods may properly be adopted except that an ultraviolet screening powder of the present invention is used as a part or the whole of the raw material providing ultraviolet screening property, high lubricity and water repellency described previously, no further explanation will be necessary. Examples to be described later will also be referred to.

Functions:

A powder obtained by treating partially or entirely the surfaces of spherical silica containing an ultraviolet reflecting material of an embodiment of the present invention with platy N-lauroyl-L-lysine, has of course the ultraviolet screening property, as well as excellent lubricity and skin fitness upon application and water repellency not found in the conventional ultraviolet reflecting powders, due to the synergistic effect of, particularly, the lubricity upon application inherent to the spherical silica and, particularly, the spreadability and smooth feeling on skins upon application inherent to the platy N-lauroyl-L-lysine. Therefore, when such a powder is incorporated into, or used as an ingredient of, cosmetics, it can screen ultraviolet light, improve the feeling in use and bleeding of make-up.

EXAMPLES

The present invention will be explained in more details with reference to the following examples.

Examples 1–2

(Preparation of spherical silica containing cerium oxide)

Commercially available weakly acidic cerium oxide sol "NEEDRAL U-15" (manufactured by Taki Kagaku Co., and containing 15 wt % of cerium oxide) was sprayed onto spherical silica "SILDEX" (manufactured by Asahi Glass Co., and having a mean particle diameter of 3 μm, a pore volume of 1.1 cc/g and a surface area of 300 m²/g) with stirring. The mixture was sufficiently mixed and then dried. Two kinds of spherical silica containing cerium oxide in different amounts were prepared by changing the amount of the cerium oxide sol to be sprayed.

Namely, the silica spheres of Example 1 contained 9% by weight of cerium oxide, and those of Example 2 contained 23% by weight of cerium oxide.

Examples 3–4

(Preparation of spherical silica containing titanium oxide)

Quite in the same manner as in the previous examples, except that commercially available titanium oxide sol (manufactured by Taki Kagaku Co., and containing 6 wt % of titanium oxide) was used instead of the weakly acidic cerium oxide sol (NEEDRAL U-15), two kinds of spherical silica containing different amounts of titanium oxide were prepared.

Namely, the silica spheres of Example 3 contained 8% by weight of titanium oxide, and those of Example 4 contained 20% by weight of titanium oxide.

Examples 5–8

(Surface treatment of spherical silica containing an ultraviolet reflecting material)

The four kinds of spherical silica containing an ultraviolet reflecting material prepared in the previous examples were subjected to surface treatment with platy N-lauroyl-L-lysine.

Namely, 85 parts by weight of the spherical silica containing the ultraviolet reflecting material prepared in each of Examples 1–4 and 15 parts by weight of N-lauroyl-L-lysine were taken, and surface treatment was carried out by stirring and mixing the two in a Henschel mixer for 20 min to obtain four kinds of surface treated spherical silica containing an ultraviolet reflecting material.

Namely, Example 5 relates to a powder obtained by surface-treating the powder of Example 1, Example 6, a powder obtained by treating the powder of Example 2, Example 7, a powder obtained by treating the powder of Example 3, and Example 8, a powder obtained by the treating powder of Example 4.

Example 9

(ditto)

15 g of N-lauroyl-L-lysine was dissolved in 500 ml of an aqueous solution of sodium hydroxide adjusted to pH 13. To the solution was added 85 g of the powder of Example 4 and dispersed sufficiently. It was neutralized by dropping 1N HCl with stirring to deposit the N-lauroyl-L-lysine on the surfaces of the powder. By washing out the salt formed by neutralization and recovering the product, the surface-treated silica spheres containing the ultraviolet reflecting material were prepared.

Test Example 1:

The performances of the powders prepared in Examples 1–9 were evaluated as for water repellency by the angle of contact and lubricity by the dynamic friction coefficient. The angle of contact was measured by pelleting the powder and dropping on the pellet water droplets with a microsyringe. The dynamic friction coefficient was measured by using a friction sensing tester manufactured by Kato-Tech Co. The results are shown in the following Table 1.

TABLE 1

| Specimen | Angle of contact | Dynamic friction coefficient |
| --- | --- | --- |
| Powder of Example 1 | 40° | 0.85 |
| Powder of Example 2 | 35° | 0.95 |
| Powder of Example 3 | 38° | 0.85 |
| Powder of Example 4 | 35° | 0.98 |
| Powder of Example 5 | 110° | 0.45 |
| Powder of Example 6 | 118° | 0.50 |
| Powder of Example 7 | 108° | 0.45 |
| Powder of Example 8 | 119° | 0.48 |
| Powder of Example 9 | 125° | 0.40 |

By treatment with N-lauroyl-L-lysine, the water repellency and the lubricity were outstandingly enhanced.

Example 10

(Powder foundation).

The powder ingredients (1)–(7) shown in the following Table 2 were mixed and pulverized. The mixture was transferred to a Henschel mixer, and the remaining ingredients (8)–(9) were then added thereto and mixed homogeneously. After conditioning the grain size to be uniform by sieving, the mixture was press-molded in a metal dish, to prepare a pressed powder foundation of appropriate adhesiveness and smoothness.

TABLE 2

| (1) Talc | 32.0 (wt %) |
| --- | --- |
| (2) Sericite | 30.0 |
| (3) Mica | 10.0 |
| (4) Magnesium stearate | 1.0 |
| (5) Titanium oxide | 5.0 |
| (6) Treated powder of Example 5 | 10.0 |
| (7) Coloring pigment | 4.0 |
| (8) Octyl dodecanol | 4.0 |
| (9) Silicone oil | 6.0 |
| Total | 100.0 |

Example 11

(Pressed powder)

The powder ingredients (1)–(7) shown in the following Table 3 were mixed and pulverized. The mixture was transferred to a Henschel mixer, and the remaining ingredients (8)–(9) were then added thereto and mixed homogeneously. After conditioning the grain size to be uniform by sieving, the mass was press-molded in a metal dish to prepare a pressed powder of appropriate adhesiveness and smoothness and having ultraviolet screening effect.

TABLE 3

| (1) Talc | 43.0 (wt %) |
| --- | --- |
| (2) Nylon powder | 15.0 |
| (3) Sericite | 15.0 |
| (4) Mica | 5.0 |
| (5) Magnesium stearate | 1.0 |
| (6) Treated powder of Example 8 | 15.0 |
| (7) Coloring pigment | appropriate amount |
| (8) Isostearic acid | 3.0 |
| (9) Methyl polysiloxane | 3.0 |
| Total | 100.0 |

Example 12

(Liquid foundation)

Ingredients (1)–(8), Ingredients (9)–(10) and Ingredients (11)–(13) shown in the following Table 4 were separately heated and mixed, respectively. After they were mixed and added with Ingredient (14), the resulting mixture was cooled gradually. The mixture was emulsified in a homomixer to prepare a liquid foundation of good spreadability upon application and having the ultraviolet screening effect.

TABLE 4

| | | |
|---|---|---|
| (1) | Stearic acid | 3.0 (wt %) |
| (2) | Isopropyl myristate | 9.0 |
| (3) | Liquid paraffin | 1.5 |
| (4) | Cetanol | 1.0 |
| (5) | Butyl paraben | appropriate amount |
| (6) | Coloring pigment | 2.0 |
| (7) | Treated powder of Example 7 | 6.0 |
| (8) | 4-tert-butyl-4'-methoxybenzoylmethane | 2.0 |
| (9) | Triethanol amine | 1.5 |
| (10) | Purified water | 25.0 |
| (11) | Propylene glycol | 5.0 |
| (12) | Methyl paraben | appropriate amount |
| (13) | Purified water | 27.0 |
| (14) | Bentonite (1% aqueous solution) | 15.0 |
| | Total | 100.0 |

Example 13

(Lotion)

The oil phase ingredients (1)–(7) and the aqueous phase ingredients (8)–(13) shown in the following Table 5 were separately heat-melted, respectively. The oil phase was gradually added to the aqueous phase with stirring. The mixture was emulsified in a homomixer to prepare a lotion of good spreadability and lubricity, excellent skin fitness, and refreshing feeling and having the ultraviolet screening effect.

TABLE 5

| | | |
|---|---|---|
| (1) | Liquid paraffin | 3.0 (wt %) |
| (2) | "AMITEL LGOD" (※1) | 2.2 |
| (3) | Propylene glycol monostearate "EMALEX PGMS" | 0.4 |
| (4) | POE (5) hardened castor oil "EMALEX HC-5" | 1.3 |
| (5) | POE (5) glyceryl monostearate "EMALEX GM-5" | 2.8 |
| (6) | Butyl paraben | 0.1 |
| (7) | Treated powder of Example 7 | 4.0 |
| (8) | "AMISOFT HS-11" (※2) | 0.3 |
| (9) | Carboxyvinyl polymer "CARBOPOLE 941" | 0.2 |
| (10) | Sodium hydroxide | 0.08 |
| (11) | 1,3-butylene glycol | 5.0 |
| (12) | Methyl paraben | 0.2 |
| (13) | Purified water | 78.72 |
| | Total | 100.0 |

(※1) Dioctyl dodecyl lauroyl glutamate manufactured by Nippon Emulsion Co.
(※2) Sodium N-hardened tallow fatty acid acyl-L-glutamate manufactured by Ajinomoto Co.

Example 14

(Lip stick)

Ingredients (1)–(9) shown in the following Table 6 were heat-melted. To the melted mass was added the pigment ingredients (10)–(14) stirred and mixed in a high speed mill. The mixture was kneaded with rolls. Subsequently, it was heat-melted again, defoamed and then molded to prepare a lip stick of appropriate spreadability and smoothness and having the ultraviolet screening effect.

TABLE 6

| | | |
|---|---|---|
| (1) | Carnauba wax | 2.0 (wt %) |
| (2) | Candelilla wax | 6.5 |
| (3) | Bee wax | 5.5 |
| (4) | Hardened castor oil | 2.0 |
| (5) | Liquid lanolin | 16.8 |
| (6) | Microcrystalline wax | 3.0 |
| (7) | Octyl dodecanol | 15.0 |
| (8) | Octyl dodecyl myristate | 10.0 |
| (9) | Castor oil | 23.2 |
| (10) | Pearl pigment | 2.0 |
| (11) | Titanium oxide | 1.5 |
| (12) | Treated powder of Example 7 | 9.0 |
| (13) | Red iron oxide | 1.3 |
| (14) | Red #202 | 2.2 |
| | Total | 100.0 |

Example 15

(Skin cream)

The oil phase ingredients (1)–(8) and the aqueous phase ingredients (9)–(12) shown in the following Table 7 were separately heat-melted, respectively, and the aqueous phase mass was added to the oil phase mass. The mixture was gradually cooled while being stirred in a homomixer, to prepare a skin cream of reduced feeling of friction after application and having the ultraviolet screening effect.

TABLE 7

| | | |
|---|---|---|
| (1) | Liquid paraffin | 17.0 (wt %) |
| (2) | Cetanol | 3.0 |
| (3) | Propylene glycol monostearate | 1.0 |
| (4) | Self-emulsifible glycerine monostearate (HLB 5.0) | 3.0 |
| (5) | POE (10) monostearic acid | 2.0 |
| (6) | POE (30) monostearic acid | 1.0 |
| (7) | Butyl paraben | 0.1 |
| (8) | Treated powder of Example 7 | 10.0 |
| (9) | 1,3-butylene glycol | 5.0 |
| (10) | "AMISOFT HS-11" | 0.3 |
| (11) | Methyl paraben | 0.2 |
| (12) | Purified water | 57.4 |
| | Total | 100.0 |

Example 16

(Cream rinse)

The oil phase ingredients (1)–(7) and the aqueous phase ingredients (8)–(12) shown in the following Table 8 were separately heat-melted, respectively, and the aqueous phase mwss were added to the oil phase mass. The mixture was emulsified in a homomixer. It was gradually cooled with paddle-stirring to 30° C. to prepare a cream rinse having the ultraviolet screening effect.

TABLE 8

| | | |
|---|---|---|
| (1) | Liquid paraffin | 2.6 (wt %) |
| (2) | Myristic acid (NAA 142) | 0.5 |
| (3) | Cetanol "Conol 30C" | 1.5 |
| (4) | "EMALEX GMS-35RT"(※1) | 3.2 |
| (5) | "PIROTEL GPI-25"(※2) | 0.4 |
| (6) | "AMITEL LGOD-2"(※3) | 1.0 |
| (7) | Treated powder of Example 7 | 3.0 |
| (8) | "CAE" (※4) | 1.0 |
| (9) | Glycerin | 2.0 |

TABLE 8-continued

| | | |
|---|---|---|
| (10) | Purified water | 84.5 |
| (11) | Perfume | 0.3 |
| | Total | 100.0 |

(※1) Self-emulsifiable glycerin monostearate
(※2) Polyoxyethylene glyceryl pyroglutamate isostearate manufactured by Nippon Emulsion Co.
(※3) Dipolyoxyethylene octyldodecyl ether lauroyl glutamate
(※4) N-palm oil fatty acid acyl-L-arginine ethyl DL-pyrrolidone carboxylic acid salt manufactured by Ajinomoto Co., Inc.

Example 17

(Sun screen cream)

The oil phase ingredients (1)–(4) shown in the following Table 9 were heated and mixed and stirred till the powder was sufficiently dispersed. Then, the aqueous phase ingredients (5)–(8) were heated and mixed. Both the phase masses were mixed and stirred in a homomixer to prepare a sun screen cream.

TABLE 9

| | | |
|---|---|---|
| (1) | Treated powder of Example 9 | 5.0 (wt %) |
| (2) | Glycerin tri (caprylic, capric acid) | 18.0 |
| (3) | Stearic acid | 20.0 |
| (4) | 2-ethylhexyl 4-(3,4-dimethoxyphenyl)-methylene)-2,5-dioxo-1-imidazolidinepropionate | 2.0 |
| (5) | Triethanol amine | 6.0 |
| (6) | Sorbitol | 4.0 |
| (7) | Methyl paraben | 0.2 |
| (8) | Purified water | the balance |
| | Total | 100.0 |

Examples 18–19

(Preparation of spherical silica containing finely particulate zinc oxide)

Zinc oxide colloid sol, dispersed with a beads mill, was added to spherical silica "SILDEX" (manufactured by Asahi Glass Co., Ltd., and having a mean particle diameter of 5 μm, a pore volume of 1.1 cc/g, and a surface area of 300 m²/g), and the obtained mixture was filtered, washed and dried. Two kinds spherical silica containing different amounts of zinc oxide were prepared by changing the amount of the zinc oxide colloid sol to be added.

Namely, the silica spheres of Example 18 contained 15% by weight of zinc oxide, and those of Example 19 contained 85% by weight of zinc oxide.

Examples 20–21

(Surface treatment of spherical silica containing finely particulate zinc oxide)

Each of the finely particulate spherical silica containing particutate zinc oxide prepared in the previous examples was surface treated with platy N-lauroyl-L-lysine.

Namely, 50 parts by weight of the spherical silica containing finely particulate zinc oxide prepared in each of Examples 18–19 and 50 parts by weight of N-lauroyl-L-lysine were taken, and surface treatment was carried out by stirring and mixing the two in a Henschel mixer for 20 min to obtain two kinds of surface treated spherical silica containing finely particulate zinc oxide.

Namely, Example 20 relates to the powder obtained by surface treating the product of Example 18 and Example 21 relates to the powder obtained by surface treating the product of Example 19.

Example 22

(Sun screen lotion)

The oil phase ingredients (1)–(12) and the aqueous phase ingredients (13)–(17) shown in the following Table 10 were separately heat-mixed, respectively. The aqueous phase mass was added to the oil phase mass, and the mixture was emulsified in a homomixer to prepare a sunscreen lotion of good spreadability upon application.

TABLE 10

| | | |
|---|---|---|
| (1) | Liquid paraffin | 9.5 (wt %) |
| (2) | Glyceryl trioctaonate | 2.5 |
| (3) | Propylene glycol monostearate | 0.3 |
| (4) | 4-tert-butyl-4'-methoxydibenzoyl methane | 2.0 |
| (5) | Di(cholesteryl, behenyl, octyldodecyl) lauroyl glutamate | 2.5 |
| (6) | Silicone oil | 0.1 |
| (7) | Behenyl alcohol | 0.5 |
| (8) | Glycerine monostearate | 1.0 |
| (9) | POE(10) monostearate | 3.0 |
| (10) | Propylene glycol | 2.0 |
| (11) | Powder of Example 20 | 3.0 |
| (12) | Butyl paraben | 0.1 |
| (13) | Carboxyvinyl polymer (aqueous 1% solution) | 30.0 |
| (14) | Propylene glycol | 5.0 |
| (15) | Sodium hardened tallow fatty acid acyl glutamate | 0.5 |
| (16) | Methyl paraben | 0.1 |
| (17) | Purified water | balance |
| | Total | 100.0 |

Example 23

(Liquid foundation)

The oil phase ingredients (1)–(6) shown in the following Table 11 were heated and mixed. The powder ingredients (7)–(11) were mixed uniformly in a mixer. The powder mass was added to, and dispersed in, the oil phase mass. The mixture being stirred in a homomixer was gradually added with the aqueous phase ingredients (12)–(15) previously heat-mixed and emulsified to prepare a liquid foundation of good spreadability and having the ultraviolet preventing effect.

TABLE 11

| | | |
|---|---|---|
| (1) | Octamethyl cyclotetrasiloxane | 17.0 (wt %) |
| (2) | Cetyl octanoate | 6.0 |
| (3) | Trigylceryl diisostearate | 1.5 |
| (4) | 2-ethylhexyl 4-(3,4-dimethoxyphenyl-methylene)-2,5-dioxo-1-imidazolizine-propionete | 8.0 |
| (5) | Di(cholesteryl, behenyl, octyldodecyl) lauroyl glutamate | 2.0 |
| (6) | POE(5) glyceryl triisostearate | 5.0 |
| (7) | Powder of Example 21 | 5.0 |
| (8) | Titanium dioxide | 11.0 |
| (9) | Talc | 6.0 |
| (10) | Organic bentonite | 0.5 |
| (11) | Coloring pigment | 5.0 |
| (12) | 1,3-butylene glycol | 5.0 |
| (13) | Ethyl alcohol | 7.0 |
| (14) | Methyl paraben | 0.1 |
| (15) | Purified water | balance |

TABLE 11-continued

| Total | 100.0 |

Effects of the Invention:

The ultraviolet screening powder of the present invention has excellent spreadability, lubricity, smooth feeling and adhesiveness and is also excellent in water repellency. Further, cosmetics having the powder blended therewith have the ultraviolet screening effect, as well as good spreadability upon application, lubricity upon application, smooth feeling on skins, good contact with skins, satisfactory water proofness and are also excellent in the effect of preventing the bleeding of make-up.

What is claimed is:

1. An ultraviolet screening powder comprising:

porous spherical silica particles having an average particle diameter of 1 to 50 µm, a pore volume of from 0.01 to 3 cc/g, 5 to 300% by weight, based on said silica, of an ultraviolet reflecting metal oxide selected from the group consisting of titanium oxide, zinc oxide, cerium oxide and mixtures thereof, and 0.05 to 90% by weight, based on said silica, of platy N-lauroyl-L-lysine of about 1 to 30 µm.

2. The ultraviolet screening powder of claim 1, wherein the pore volume of said silica is from 0.5 to 2.5 cc/g, its average particle diameter is 2 to 20 µm, the amount of ultraviolet reflecting metal oxide is from 20 to 100% by weight based on said silica and the amount of N-lauroyl-L-lysine is from 0.5 to 75% by weight, based on said silica.

3. The ultraviolet screening powder of claim 1, containing two or more metal oxides.

4. A cosmetic comprising an ultraviolet screening powder of claim 1, 2 or 3.

* * * * *